United States Patent
Basheer et al.

(10) Patent No.: US 9,802,911 B1
(45) Date of Patent: *Oct. 31, 2017

(54) METHOD FOR FORMING FURANONE FROM BIOMASS

(71) Applicant: KING FAHD UNIVERSITY OF PETROLEUM AND MINERALS, Dhahran (SA)

(72) Inventors: Chanbasha Basheer, Dhahran (SA); Ahmed Abdi Hassan, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 15/652,681

(22) Filed: Jul. 18, 2017

Related U.S. Application Data

(63) Continuation of application No. 15/370,015, filed on Dec. 6, 2016, now Pat. No. 9,751,849.

(51) Int. Cl.
| | | |
|---|---|---|
| *C07D 307/00* | (2006.01) | |
| *C07D 307/60* | (2006.01) | |
| *B01J 19/12* | (2006.01) | |

(52) U.S. Cl.
CPC .......... *C07D 307/60* (2013.01); *B01J 19/127* (2013.01); *B01J 2219/0877* (2013.01); *B01J 2219/0892* (2013.01); *B01J 2219/1203* (2013.01)

(58) Field of Classification Search
CPC ................. C07D 307/60; B01J 19/127; B01J 2219/1203; B01J 2219/0892; B01J 2219/0877
USPC ....................................................... 549/313
See application file for complete search history.

(56) References Cited

U.S. PATENT DOCUMENTS

| | | |
|---|---|---|
| 6,645,432 B1 | 11/2003 | Anderson et al. |
| 6,660,132 B1 | 12/2003 | Demuth et al. |
| 8,877,930 B2 | 11/2014 | Bedore et al. |
| 2005/0245628 A1 | 11/2005 | Hubel et al. |
| 2007/0197801 A1 | 8/2007 | Bolk et al. |
| 2012/0003734 A1 | 1/2012 | Mohr et al. |

FOREIGN PATENT DOCUMENTS

| | | |
|---|---|---|
| KR | 10-2012-0095463 | 8/2012 |
| KR | 10-2013-0138703 | 12/2013 |
| WO | 2014/027364 A1 | 2/2014 |

(Continued)

OTHER PUBLICATIONS

Taichi Kano, et al., "Metal-Free Enantioselective Hydroxyamination of Aldehydes with Nitrosocarbonyl Compounds Catalyzed by an Axially Chiral Amine", J. Am. Chem. Soc., vol. 135 No. 48, (2013), Abstract only.

(Continued)

*Primary Examiner* — T. Victor Oh
(74) *Attorney, Agent, or Firm* — Oblon, McClelland, Maier & Neustadt, L.L.P.

(57) ABSTRACT

A method of photooxygenating furfural in a photooxygenating system, whereby a liquid mixture comprising furfural, a photosensitizer, and a reaction solvent is passed through a reaction section of the photooxygenating system, wherein the liquid mixture is exposed to solar radiation, while a portion of the furfural is oxidized in presence of the photosensitizer and a furanone compound is produced. Various embodiments of the photocatalytic water splitting reactor, and the water splitting system are also provided.

16 Claims, 9 Drawing Sheets

(56) References Cited

FOREIGN PATENT DOCUMENTS

WO    2015/179888 A1    12/2015
WO    2016/011468 A1    1/2016

OTHER PUBLICATIONS

Hongjun Liu, et al., "Organic dye photocatalyzed α-oxyamination through irradiation with visible light", Green Chemistry, vol. 12, (2010), pp. 953-956.
Peter Schroll, et al., "Photocatalytic α-Oxyamination of Stable Enolates, Silyl Enol Ethers, and 2-Oxoalkane Phosphonic Esters", European Journal of Organic Chesmisty, (2015), pp. 309-313.
Nsubuga, et al., "Isolation, characterization, and evaluation of photochemical potential of rice hsk-based furfural via continuous flow reactor", Journal of Environmental Chemical Engineering, 4, 2016, p. 857-863, which was available online Dec. 29, 2015.

METHOD FOR FORMING FURANONE FROM BIOMASS

CROSS-REFERENCE TO RELATED APPLICATIONS

The present application is a continuation of Ser. No. 15/370,015, now allowed, having a filing date of Dec. 6, 2016.

STATEMENT OF ACKNOWLEDGEMENT

This project was funded by King Abdul Aziz City for Science and Technology through the Science and Technology Unit at King Fand University of Petroleum and Minerals (KFUPM) under project number 13-ENE277-04), as a part of the National Science Technology and Innovation Plan.

BACKGROUND OF THE INVENTION

Technical Field

The present invention relates to a method of photooxygenating furfural using a photooxygenating system to produce a furanone compound.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Ecological sustainability concern and surging crude oil prices have amplified industrial interest for renewable biomass resources [K. Tekin, S. Karagöz, S. Bektaş, Hydrothermal conversion of woody biomass with disodium octaborate tetrahydrate and boric acid, Ind. Crops Prod. 49 (2013) 334-340]. Of the various biomasses with abundant and renewable energy sources, rice husk is not only a cheap potential source of energy, but also a value-added by-product [L. T. Vlaev, I. G. Markovska, L. A. Lyubchev, Non-isothermal kinetics of pyrolysis of rice husk, Thermochim. Acta 406 (2003) 1-7]. Its annual worldwide output is in million tons [Q. Lu, X. Yang, X. Zhu, Analysis on chemical and physical properties of bio-oil pyrolyzed from rice husk, J. Anal. Apple Pyrolysis 82 (2008) 191-198], and its major components are hemicellulose (19%), cellulose (40%), silica (17%) and lignin (16%) [R. Suxia, X. Haiyan, Z. Jinling, L. Shunqing, H. Xiaofeng, L. Tingzhou, Furfural production from rice husk using sulfuric acid and a solid acid catalyst through a two-stage process, Carbohydr. Res. 359 (2012) 1-6]. Agricultural waste-based lignocellulosic materials rich in pentosans have generally been preferred for producing value-added chemicals [O. Yemis, G. Mazza, Acid-catalyzed conversion of xylose, xylan and straw into furfural by microwave-assisted reaction, Bioresour. Technol. 102 (2011) 7371-7378] since they are homogeneous and readily available in large quantities from cheap sources [I. Harry, H. Ibrahim, R. Thring, R. Idem, Catalytic subcritical water liquefaction of flax straw for high yield of furfural, Biomass Bioenergy 71 (2014) 381-393]. Biomass resources are a perfect choice to replace the petroleum feedstock [A. J. Ragauskas, C. K. Williams, B. H. Davison, G. Britovsek, J. Cairney, C. A. Eckert, et al., The path forward for biofuels and biomaterials, Science 311 (2006) 484-489]. They are even considered viable options for improving energy security and reducing greenhouse-gas emissions thus addressing the recurrent treatment challenges of waste streams from process plants [C. Di Blasi, C. Branca, A. Galgano, Biomass screening for the production of furfural via thermal decomposition, Ind. Eng. Chem. Res. 49 (2010) 2658-2671]. However, their effective utilization is limited by the quest in developing inexpensive processing methods that are capable of transforming the abundantly available carbohydrate moieties into value-added chemicals [J. N. Chheda, Y. Roman-Leshkov, J. A. Dumesic, Production of 5-hydroxymethylfurfural and furfural by dehydration of biomass-derived mono- and poly-saccharides, Green Chem. 9 (2007) 342]. Recently, furfural has received renewed attention as a potential renewable platform for the production of biochemicals and biofuels [C. M. Cai, T. Zhang, R. Kumar, C. E. Wyman, Integrated furfural production as a renewable fuel and chemical platform from lignocellulosic biomass, J. Chem. Technol. Biotechnol. 89 (2014) 2-10]. Furfural (2-furaldehyde) is a versatile furan platform comprised of a heteroaromatic furan ring and an aldehyde group and is reported to be the sole precursor for compounds containing furoyl (furoyl glycine and 2-furoylchloride), furyl (furanones and furans), and furfurylidene radicals [O. Yemis, G. Mazza, Acid-catalyzed conversion of xylose, xylan and straw into furfural by microwave-assisted reaction, Bioresour. Technol. 102 (2011) 7371-7378]. It is asserted to be among the top 30 high-value bio-based chemicals [T. Werpy, G. Petersen, Top Value Added Chemicals from Biomass Volume I—Results of Screening for Potential Candidates from Sugars and Synthesis Gas Top Value Added Chemicals From Biomass Volume I: Results of Screening for Potential Candidates, US Department of Energy, Technical report, DOE/GO-102004-1992 August 2004], and its demand is greatly felt in fields such as petrochemical refining, agrochemical, pharmaceutical and plastics industries [A. S. Dias, S. Lima, M. Pillinger, A. A. Valente, Acidic cesium salts of 12-tungstophosphoric acid as catalysts for the dehydration of xylose into furfural, Carbohydr. Res. 341 (2006) 2946-2953].

Furfural production involves both acidic hydrolysis and dehydration through either one or two stage process using either one or multiple reactors [R. Suxia, X. Haiyan, Z. Jinling, L. Shunqing, H. Xiaofeng, L. Tingzhou, Furfural production from rice husk using sulfuric acid and a solid acid catalyst through a two-stage process, Carbohydr. Res. 359 (2012) 1-6; O. Yemiş, G. Mazza, Acid-catalyzed conversion of xylose, xylan and straw into furfural by microwave-assisted reaction, Bioresour. Technol. 102 (2011) 7371-7378] as shown in FIG. 2 [K. Yan, G. Wu, T. Lafleur, C. Jarvis, Production, properties and catalytic hydrogenation of furfural to fuel additives and value-added chemicals, Renew. Sustain. Energy Rev. 38 (2014) 663-676]. In most research reports, a two-stage process is utilized since it generates higher furfural yield [V. Punsuvon, P. Vaithanomsat, K. Iiyama, Simultaneous production of a-cellulose and furfural from bagasse by steam explosion pretreatment, Maejo Int. J. Sci. Tech 2 (2008) 182-191].

The currently used batch and continuous furfural production processes are energy intensive, expensive, environmentally unfriendly and cause acid wastes [O. Yemis, G. Mazza, Acid-catalyzed conversion of xylose, xylan and straw into furfural by microwave-assisted reaction, Bioresour. Technol. 102 (2011) 7371-7378]. Hence, the recent trend in furfural research is geared towards novel production processes that are both inexpensive and environmentally appealing. The techniques of supercritical fluid extraction [W. Sangarunlert, P. Piumsomboon, S. Ngamprascrtsith, Furfural production by acid hydrolysis and supercritical carbon dioxide extraction from rice husk, Korean J. Chem. Eng. 24 (2007) 936-941], pressurized solvent extraction [H. K. Ong, M. Sashikala, Identification of furfural synthesized from pentosan in rice husk, J. Trop. Agric. Food Sci. 35 (2007) 305-312] and microwave-assisted extraction method [O. Yemis, G. Mazza, Acid-catalyzed conversion of xylose, xylan and straw into furfural by microwave-assisted reaction, Bioresour. Technol. 102 (2011) 7371-7378] have been accepted as novel methods in furfural production.

Conversely, the use of abundant sunlight as a clean source of energy to initiate chemical transformations has attracted the attention of synthetic organic photochemists, since a variety of photoreactions high in selectivity, chemical yields and photon efficiencies are generated [M. Oelgemöller, O. Shvydkiv, Recent advances in microflow photochemistry, Molecules 16 (2011) 7522-7550]. Moreover, sunlight is a cheap, environmental friendly, plentiful and continuous renewable source of clean energy. However, despite these significant merits, organic synthesis still remains highly resource- and labor-intensive [P. T. Anastas, M. M. Kirchhoff, Origins, current status, and future challenges of green chemistry, Acc. Chem. Res. 35 (2002) 686-694]. Recently, microphotochemistry has been utilized in synthetic organic chemistry since it combines the advantages of miniaturized microflow systems with organic photochemistry [D. Webb, T. F. Jamison, Continuous flow multi-step organic synthesis, Chem. Sci. 1 (2010) 675]. The continuous removal of the product mixture from the irradiated area reduces secondary photoreactions, whereas the thin reaction channels enable efficient penetration of light through the reaction mixture (as dictated by the Beer-Lambert law) [S. Aida, K. Terao, Y. Nishiyama, K. Kakiuchi, M. Oelgemöller, Microflow photochemistry—a reactor comparison study using the photochemical synthesis of terebic acid as a model reaction, Tetrahedron Lett. 53 (2012), 5578-5581].

In addition, organic dyes as the photosensitizer in photochemical reactions are cheap, easy to prepare, more environmentally friendly and present a practical alternative to inorganic photocatalysts [H. Liu, W. Feng, C. W. Kee, Y. Zhao, D. Leow, Y. Pan, et al., Organic dye photocatalyzed a-oxyamination through irradiation with visible light, Green Chem. 12 (2010) 953]. The application of light-induced reactions in continuous flow microreactors combines the advantages of microreactor technology with sunlight photons as clean and traceless reagents [S. Hejda, M. Drhova, J. Kristal, D. Buzek, P. Krystynik, P. Kluson, Microreactor as efficient tool for light induced oxidation reactions, Chem. Eng. J. 255 (2014) 178-184]. In addition, microreactors offer higher spatial illumination homogeneity and better light penetration throughout the entire reactor [T. Aillet, K. Loubiere, O. Dechy-Cabaret, L. Prat, Photochemical synthesis of a cage compound in a microreactor: rigorous comparison with a batch photoreactor, Chem. Eng. Process.: Process intensif. 64 (2013) 38-47].

In view of the forgoing, one objective of the present invention is to provide a method of synthesizing a furanone compound (e.g., 5-hydroxy-2-(5H)-furanone) by photooxygenating furfural, which is extracted from rice husk, using an in-house fabricated quartz capillary microreactor (0.5 mm diameter and 3 m length).

BRIEF SUMMARY OF THE INVENTION

According to a first aspect, the present disclosure relates to a method of producing a furanone compound, involving i) extracting furfural from rice husk, i) mixing the furfural, a photosensitizer, and a reaction solvent in a vessel to form a liquid mixture, iii) flowing at least a portion of the liquid mixture through a reaction section of a flow reactor, while concurrently exposing the liquid mixture to sunlight to oxidize the furfural to form the furanone compound.

In one embodiment, the method of producing a furanone compound further involves i) collecting the liquid mixture in the vessel, ii) repeating the flowing and the collecting until the liquid mixture reaches a predetermined furanone concentration.

In one embodiment, the extracting comprises treating the rice husk with a mineral acid in a microwave.

In one embodiment, the extracting comprises hydrolyzing the rice husk with a mineral acid in an autoclave.

In one embodiment, the extracting comprises treating the rice husk with a mineral acid in a reflux system.

In one embodiment, the photosensitizer is an organic dye.

In one embodiment, a concentration of the photosensitizer in the liquid mixture is in the range of 4-40 g/l.

In one embodiment, the liquid mixture comprises 0.2-2.5 g of the photosensitizer per 1 ml of the furfural.

In one embodiment, the reaction solvent is at least one selected from the group consisting of water, methanol, ethanol, acetonitrile, dichloromethane, tetrahydrofuran, and toluene.

In one embodiment, the reaction solvent is methanol.

In one embodiment, a concave mirror is located under the reaction section, wherein the concave mirror has a focal point for focusing sunlight onto the reaction section.

In one embodiment, the reaction section is exposed to sunlight for 2-12 hours.

In one embodiment, the reaction section of the flow reactor has a spiral shape.

In one embodiment, the method of producing a furanone compound further involves i) separating the furanone compound from the liquid mixture in a separator to form a furanone compound stream and a recycle stream, ii) delivering at least a portion of the recycle stream to the vessel.

In one embodiment, the method of producing a furanone compound further involves stirring the liquid mixture in the vessel with an agitator.

In one embodiment, the liquid mixture in the vessel is maintained at a temperature below 35° C. to prevent acetalization.

In one embodiment, an illuminance received by the liquid mixture inside the vessel is less than 0.001 lux.

In one embodiment, an irradiance received by the liquid mixture inside the vessel is less than 300 W/m$^2$.

According to a second aspect, the present disclosure relates to a photooxygenating system, involving i) a flow reactor with a reaction section in the form of a spiral or coil having a first end and a second end and a mirror located underneath the reaction section, wherein a reflecting side of the mirror faces the reaction section to enhance solar radiation, ii) a vessel with an internal cavity, a liquid inlet port, and a liquid outlet port, wherein the liquid outlet port is fluidly connected to the first end of the reaction section via a first liquid line, and the liquid inlet port is fluidly connected to the second end of the reaction section via a second liquid line, iii) a pump for delivering a liquid mixture comprising furfural, a photosensitizer, and a reaction solvent from the vessel to the reaction section, wherein the furfural is converted into a furanone compound, and returning the liquid mixture to the vessel.

In one embodiment, the photooxygenating system further involves a separator which is fluidly connected to a discharge port of the vessel via a discharge line, wherein the separator is configured to separate the furanone compound from the liquid mixture.

In one embodiment, the reaction section is made of quartz.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1A:
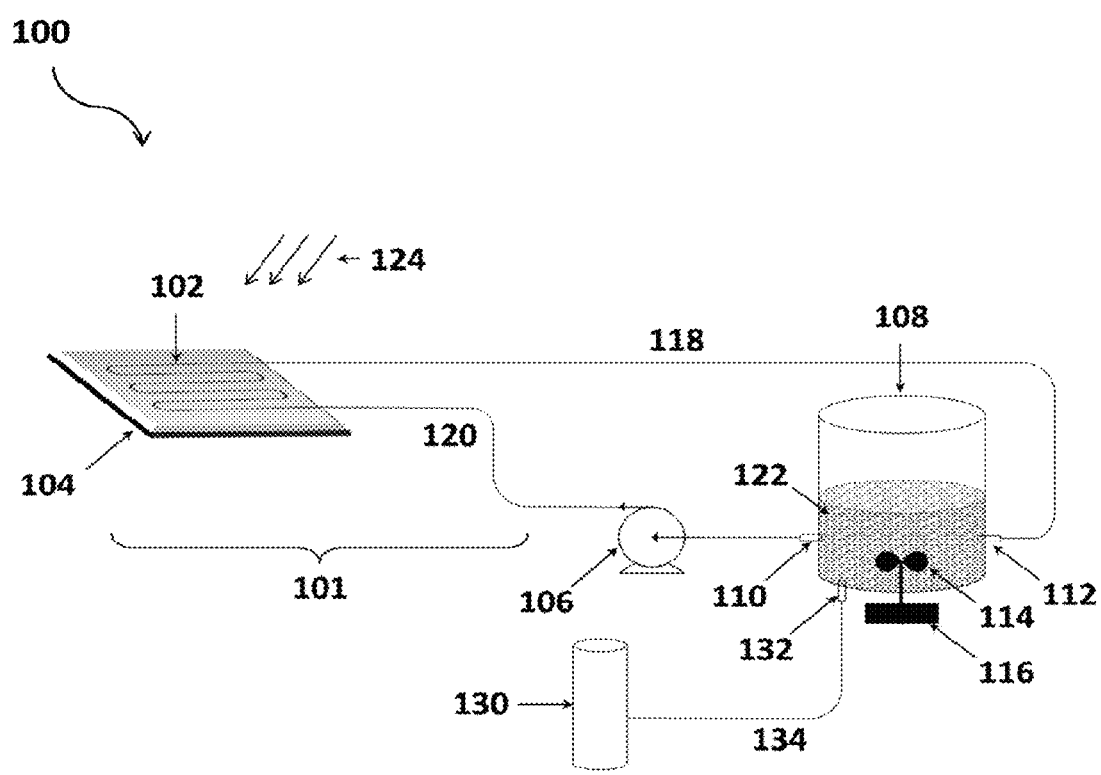
FIG. 1A illustrates a flow reactor which is fluidly connected to a vessel via a set of liquid lines.

Referring now to the drawings, wherein like reference numerals designate identical or corresponding parts throughout the several views.

According to a first aspect the present disclosure relates to a method of producing a furanone compound involving extracting furfural from rice husk. The furanone compound may be, for example, 5-hydroxy-2(5H)-furanone that has a chemical formula of $C_4H_4O_3$. The method may produce the furanone compound having a purity of at least 90 wt %, preferably 92 wt %, or preferably 94 wt %, or preferably 96 wt %, or preferably 98 wt %, or preferably 99 wt % of 5-hydroxy-2(5H)-furanone. In one embodiment, impurities may be present in the rice husk extract in an amount of less than 10 wt %, preferably less than 5 wt %, more preferably less than 2 wt %, even more preferably less than 1 wt %, wherein wt % is based on the total weight of the extract including the solvent. In one embodiment, the impurities include, but are not limited to 2-furanone, furaneol, furfural, methanol, ethanol, and/or water. The 5-hydroxy-2(5H)-furanone compound may convert to its isomer form (i.e. cis-β-formylacrylic acid), via a reversible tautomerization reaction. Tautomerization reaction refers to interconverting reactions that readily convert an organic compound to its isomeric compound. Therefore, cis-β-formylacrylic acid is also referred to herein as 5-hydroxy-2(5H)-furanone.

Rice husk refers to a hard protecting covering of rice grains that is separated from the rice grains in a milling process. Rice husk may comprise hemicellulose, cellulose, silica, lignin, and pentose sugar. In one embodiment, the rice husk comprises at least 15%, preferably at least 18%, preferably at least 20% hemicellulose, at least 30%, preferably at least 35%, preferably at least 40% cellulose, at least 10%, preferably at least 15%, preferably at least 17% silica, and at least 15%, preferably at least 18%, preferably at least 20% lignin, each component by weight relative to the total weight of the rice husk. The rice husk as used herein may refer to a ground and/or pulverized rice husk having a particle size less than 3 mm, preferably less than 2 mm, and more preferably less than 1 mm. In one embodiment, 10-40%, preferably 15-35%, or preferably 20-30%, or preferably about 25% by weight of rice husk comprises pentose sugar, wherein the pentose sugar in rice husk is present in the form of glucose, xylose, and arabinose. In a preferred embodiment, only xylose and arabinose converts to the furfural. In another embodiment, furfuryl derivatives (i.e. compounds containing furyl, furfuryl, furoyl, and furfurylidene) are produced during extracting furfural from rice husk. Exemplary furfural derivatives include, but are not limited to furfuryl alcohol, furan, hydroxymethyl furfural, tetrahydrofurfuryl alcohol, 3,4-dihydro-2H-pyran, furfurylamine, tetrahydrofurfurylamine, 2-methylfuran, 2-methyltetrahydrofuran, and furoic acid. In another embodiment, extracting furfural from the rice husk is accompanied with production of methanol, and acetic acid. In one embodiment, the method of producing the furanone compound may co-produce furanone derivatives including 4-(2-(2-aminoethoxy)-2,5-dimethyl-3(2H)-furanone, and 5-(2-(2-aminoethoxy)-ethoxy)methyl)-2(5H)-furanone.

Alternatively, in one embodiment, furfural is extracted from bagasse, wheat straw, and/or corn cob, corn stalk, sunflower hull, wood, olive stone, and sugar cane bagasse.

In one embodiment, the extracting comprises treating the rice husk with a mineral acid in a microwave to form a microwave treated mixture. Exemplary mineral acids may include, but are not limited to nitric acid, sulfuric acid, phosphoric acid, boric acid, hydrofluoric acid, hydrobromic acid, and perchloric acid. In a preferred embodiment, the mineral acid is hydrochloric acid having a concentration in the range of 0.05-0.5 M, preferably 0.1-0.2 M, more preferably 0.1 M. In one embodiment, 0.12 g, or preferably 0.5-1.5 g, even more preferably 1 g of the rice husk is mixed with 10-40 ml of 0.1 M hydrochloric acid, preferably 10-30 ml of 0.1 M hydrochloric acid, more preferably 20 ml of 0.1 M hydrochloric acid in a vessel to form a reaction mixture. The vessel is preferably made of or coated with PTFE. An agitator present in the vessel may stir the reaction mixture for at least 1 min, preferably at least 3 min, more preferably at least 4 min. The vessel containing the reaction mixture may further be positioned in the microwave, which may be equipped with a temperature-control system, wherein a preset temperature, a cooling/heating ramp rate, and residence time can be defined using a computer interface connected to the temperature-control system. In one embodiment, the reaction mixture is raised to a reaction temperature in the range of 140-220° C., preferably 160-200° C., more preferably 180° C., wherein the reaction temperature is reached in a heating ramp time in the range of 5-15 min, preferably 8-12 min, more preferably 10 min.

The reaction mixture may be maintained at the reaction temperature for a residence time in the range of 10-30 min, preferably 15-25 min, more preferably 18-22 min, and even more preferably 20 min. The reaction mixture may further be cooled down to room temperature (i.e. 20-30° C., preferably 25-28° C.) in a cooling ramp time in the range of 35-45 min, preferably 38-42 min, more preferably 40 min. In one embodiment, the microwave treated mixture is filtered and further passed to a separatory funnel, wherein furfural is extracted from the microwave treated mixture via a liquid-liquid extraction process. In one embodiment, chloroform, dichloromethane, dichloroethane, and the like are used to extract the furfural. In another embodiment, the furfural is further refined using a rotary evaporator. In one embodiment, furfural that is produced by treating the rice husk with hydrochloric acid in the microwave has a purity of at least 90 wt %, preferably at least 92 wt %, or preferably at least 94 wt %, or preferably at least 96 wt %, or preferably at least 98 wt %, or preferably at least 99 wt %. In one embodiment, yield of furfural production from treating the rice husk in the microwave is in the range of 50-80%, preferably 60-70%, more preferably about 68%, wherein yield is calculated based on the total weight of the pentose sugars present in the rice husk.

Figure 2:
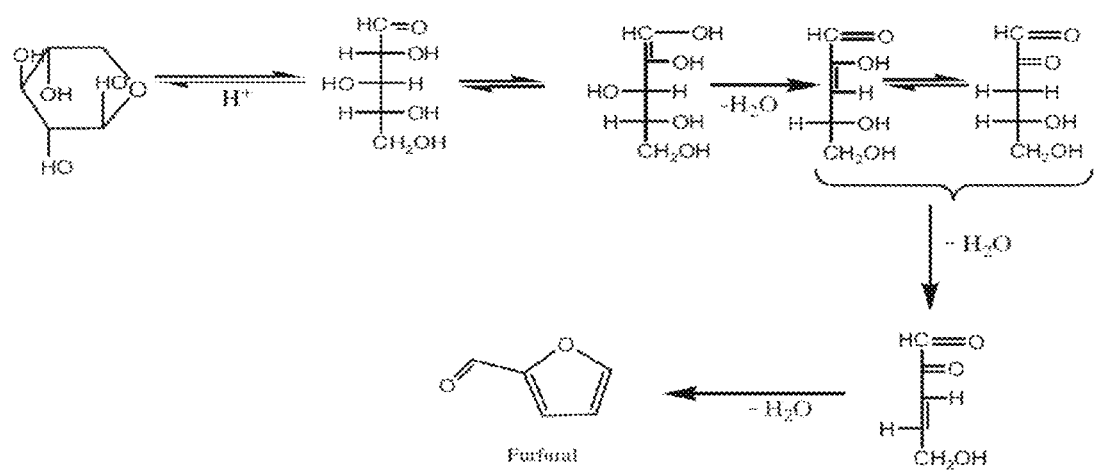
FIG. 2 represents a reaction schematic for producing furfural from pentose sugar [K. Yan, G. Wu, T. Lafleur, C. Jarvis, Production, properties and catalytic hydrogenation of furfural to fuel additives and value-added chemicals, Renew. Sustain. Energy Rev. 38 (2014) 663-676].

In one embodiment, the extracting comprises hydrolyzing the rice husk with a mineral acid in an autoclave. Autoclave refers to a pressure chamber used to carry out reactions and processes that require elevated temperature and pressure different than ambient pressure (i.e. 1 atm) and temperature (i.e. about 25° C.). Exemplary mineral acids may include, but are not limited to hydrochloric acid, nitric acid, phosphoric acid, boric acid, hydrofluoric acid, hydrobromic acid, and perchloric acid. In a preferred embodiment, the mineral acid is sulfuric acid having a concentration in the range of 0.05-1.5 M, preferably 0.5-1.2 M, more preferably 1.0 M. In one embodiment, 1-20 g, or preferably 5-15 g, even more preferably 8 g of the rice husk is mixed with 10-400 ml of 1.0 M sulfuric acid, preferably 50-200 ml of 1.0 M sulfuric acid, more preferably 100 ml of 1.0 M sulfuric acid to form a pulverized rice husk blend. Further, the pulverized rice husk blend is packed in the autoclave, which is made of stainless steel with a Teflon® inner lining for acid hydrolysis. In another embodiment, sealing of the autoclave is provided by metal end caps and temperature resistant rubber gaskets. The autoclave may further be placed in a pre-heated oven having a preset temperature in the range of 140-220° C., preferably 160-200° C., more preferably 180° C. for duration of 5-10 hours, preferably 6-8 hours, more preferably about 7 hours. Pentosan present in the rice husk hydrolyzes to form furfural (reaction scheme is shown in FIG. 2). The autoclave may further be removed from the pre-heated oven and may be cooled down to room temperature (i.e. 20-30° C., preferably 25-28° C.). The pulverized rice husk blend may be filtered to form a filtrate. Furfural may further be separated from the filtrate via a separatory funnel. In a preferred embodiment, the furfural is first dehydrated with a solid acid catalyst (e.g. SBA-15) and toluene, then separated via the separatory funnel, and finally refined and concentrated using a rotary evaporator. The rotary evaporator may be operated at a temperature in the range of 40-80° C., preferably 50-60° C., more preferably 55° C., and at a rotary speed of 50-100 rpm, preferably 80-90 rpm, more preferably 85 rpm. In one embodiment, furfural that is produced by treating the rice husk with sulfuric acid in the autoclave has a purity of at least 90 wt %, preferably at least 92 wt %, or preferably at least 94 wt %, or preferably at least 96 wt %, or preferably at least 98 wt %, or preferably at least 99 wt %. In one embodiment, yield of furfural production from treating the rice husk in the autoclave is in the range of 40-60%, preferably 45-55%, more preferably about 52%, wherein yield is calculated based on the total weight of the pentose sugars present in the rice husk.

In one embodiment, the extracting comprises treating the rice husk with a mineral acid in a reflux system. Exemplary mineral acids may include, but are not limited to nitric acid, sulfuric acid, phosphoric acid, boric acid, hydrofluoric acid, hydrobromic acid, and perchloric acid. In a preferred embodiment, the mineral acid is hydrochloric acid having a concentration in the range of 0.05-1.5 M, preferably 0.5-1.2 M, more preferably 1.0 M. The reflux system may include a container, preferably a three-neck flask, which is fluidly connected to a vertically oriented column and a condenser. A rice husk mixture can be prepared by mixing pulverized rice husk, sodium chloride, and the hydrochloric acid. In one embodiment, 200-300 g, preferably 250-280 g, more preferably about 265 g of pulverized rice husk is mixed with 100-600 g, preferably 300-500 g, more preferably about 400 g of sodium chloride in 1-3 L, preferably 1-2 L, more preferably 1.5 L of hydrochloric acid in the container, and the container is further heated up to a temperature in the range of 100-150° C., preferably 100-120° C., more preferably 110° C., while the rice husk mixture in the container is continuously stirred with an agitator present inside the container. In one embodiment, a distillate that formed in the condenser is collected in a flask containing chloroform. Two phases of liquid may be formed in the flask, wherein dissolved furfural in chloroform is the heavier phase that is accumulated at the bottom of the flask. In one embodiment, the furfural is further isolated from chloroform using a rotary evaporator, wherein the rotary evaporator operates at a temperature below 50° C., preferably below 45° C., more preferably below 40° C. In one embodiment, furfural that is produced by treating the rice husk with hydrochloric acid in the reflux system has a purity of at least 90 wt %, preferably at least 92 wt %, or preferably at least 94 wt %, or preferably at least 96 wt %, or preferably at least 98 wt %, or preferably at least 99 wt %. In one embodiment, yield of furfural production from treating the rice husk in the reflux system is in the range of 30-50%, preferably 35-45%, more preferably about 40%, wherein yield is calculated based on the total weight of the pentose sugars present in the rice husk.

The method of producing the furanone compound further involves mixing the furfural obtained from an extraction process described herein, a photosensitizer, and a reaction solvent in a vessel to form a liquid mixture.

Photosensitizer refers to a chemical compound that initiates a light-induced chemical reaction (e.g. photooxygenation), by absorbing electromagnetic radiation, which may be ultraviolet or visible light. Accordingly, the photosensitizer enters an excited state when exposed to light of a specific wavelength, and further reacts with either a substrate or ground state molecular oxygen, starting a cascade of energy transfer that results in an oxygenated compound.

The photosensitizer may be an organic dye. Exemplary photosensitizers include, but are not limited to Rose Bengal (or RB), Basic Blue 9, Rhodamine B, methylene blue, mesotetraphenylporphine (or TPP), polyene dye 2-cyano-5-(4-dimethylaminophenyl)penta-2,4-dienoic acid (or NKX-2553), $Ru(byp)_3Cl_2$, and $Ru(byp)_3Cl_2$-imidazolidinone. In a preferred embodiment, the photosensitizer is Rose Bengal (or RB).

Exemplary reaction solvents include, but are not limited to water, methanol, ethanol, acetonitrile, dichloromethane, tetrahydrofuran, and toluene. In a preferred embodiment, the reaction solvent is methanol.

In one embodiment, 0.2-2.5 g, preferably 0.5-1.5 g, more preferably 0.8-1 g, even more preferably about 0.9 g of Rose Bengal is dissolved in 10-100 ml, preferably 20-80 ml, more preferably 40-60 ml, even more preferably about 50 ml of methanol to form a dye solution. In another embodiment, 0.1-2 ml, preferably 0.4-1.5 ml, more preferably 0.6-1 ml, even more preferably about 0.8 ml of the furfural per 10-100 ml, preferably per 20-80 ml, more preferably per 40-60 ml, even more preferably per 50 ml of methanol is added to the dye solution to form the liquid mixture. In one embodiment, the liquid mixture comprises 0.2-2.5 g, preferably 0.5-1.5 g, more preferably 0.8-1 g, even more preferably about 0.9 g of Rose Bengal per 0.1-2 ml, preferably per 0.4-1.5 ml, more preferably per 0.6-1 ml, even more preferably per 0.8 ml of the furfural.

In one embodiment, the concentration of the photosensitizer in the liquid mixture is in the range of 0.1-100 g/l, preferably 1-80 g/l, or preferably 4-60 g/l, or preferably 4-40 g/l, or preferably about 20 g/l. In another embodiment, concentration of the Rose Bengal in the liquid mixture is in the range of 0.1-100 g/l, preferably 1-80 g/l, or preferably 4-60 g/l, or preferably 4-40 g/l, or preferably about 20 g/l.

In one embodiment, the concentration of the furfural in the liquid mixture is in the range of 0.1-5%, preferably 0.5-2%, or preferably 1-2%, or preferably about 1.5% by volume.

The mixing refers to a process, whereby predetermined amounts of the furfural, the photosensitizer, and the reaction solvent are added in the vessel and continuously stirred to form a blended mixture. In a preferred embodiment, the photosensitizer is dissolved in the reaction solvent separately to form the dye solution, and the dye solution is further mixed with the furfural. In one embodiment, temperature of the liquid mixture is raised up to 60° C., preferably up to 50° C., or preferably up to 40° C. to facilitate the mixing. In one embodiment, the vessel is pre-heated up to 60° C., preferably up to 50° C., or preferably up to 40° C. before mixing the furfural, the photosensitizer, and the reaction solvent in the vessel.

The method of producing the furanone compound further involves flowing at least a portion of the liquid mixture through a reaction section of a flow reactor, while concurrently exposing the liquid mixture to sunlight to oxidize the furfural to form the furanone compound.

"Flowing at least a portion of the liquid mixture" as used herein refers to transferring a portion of the liquid mixture from the vessel to the reaction section of the flow reactor, wherein a photooxygenation reaction takes place. Photooxygenation reaction is a light-induced oxidation reaction which is initiated by a photosensitizer. In one embodiment, flowing is carried out via a pump. In a preferred embodiment, a flow-rate control system regulates a flow rate of the liquid mixture through the reaction section, wherein the flow rate of the liquid mixture is in the range of 0.5-50 ml/min, preferably 1-30 ml/min, more preferably 10-30 ml/min, even more preferably about 20 ml/min to provide sufficient residence time of the liquid mixture in the reaction section. In one embodiment, the residence time is in the range of 1-100 min, preferably 2-50 min, more preferably 2-5 min, even more preferably about 2.5 min.

The liquid mixture is exposed to sunlight in the reaction section of the flow reactor, wherein the photosensitizer absorbs light photons to enter an excited state. The exposing may refer to placing the reaction section of the flow reactor, which is transparent, in an uncovered location under solar radiation. In one embodiment, exposing further refers to placing the reaction section of the flow reactor in an uncovered location in a partially cloudy, or a cloudy condition. In one embodiment, exposing may also refer to placing the reaction section of the flow reactor under an artificial light source in addition to or in the absence of solar radiation. Exemplary artificial light sources include, but are not limited to UV light, visible light bulb, fluorescent bulb/tube, X-ray source, γ-ray source, infrared, and microwave.

In one embodiment, the reaction section of the flow reactor is exposed to sunlight, wherein an illuminance received by the liquid mixture in the reaction section is in the range of 400-120,000 lux, preferably 10,000-100,000 lux, more preferably 30,000-100,000 lux, even more preferably 50,000-100,000 lux. In one embodiment, the reaction section of the flow reactor is exposed to sunlight, wherein an irradiance received by the liquid mixture in the reaction section is in the range of 200-1,200 W/m$^2$, preferably 300-1,000 W/m$^2$, more preferably 300-850 W/m$^2$. In one embodiment, in the absence of solar radiation the reaction section of the flow reactor is exposed to an artificial light source, wherein an irradiance received by the liquid mixture in the reaction section is in the range of 200-1,200 W/m$^2$, preferably 300-1,000 W/m$^2$, more preferably 300-850 W/m$^2$.

In one embodiment, exposing the liquid mixture to sunlight may be enhanced by placing a mirror under the reaction section of the flow reactor, wherein a reflecting side of the mirror faces the reaction section. In one embodiment, the mirror is a concave mirror having a focal point for focusing sunlight onto the reaction section.

In one embodiment, the method of producing the furanone compound preferably involves collecting the liquid mixture in the vessel, followed by flowing a portion of the liquid mixture from the vessel to the reaction section of the flow reactor. In one embodiment, the liquid mixture is continuously circulated through the flow reactor for 2-12 hours, preferably 4-10 hours, more preferably about 6 hours, wherein the reaction section is exposed to sunlight.

In one embodiment, the method of producing the furanone compound further involves repeating the flowing and the collecting until the liquid mixture reaches a predetermined furanone concentration. In one embodiment, the predetermined furanone concentration in the liquid mixture is in the range of 60-100%, preferably 70-95%, or preferably 75-90%, or preferably 80-85% by volume. In another preferred embodiment, when methanol is used as the reaction solvent in the liquid mixture, temperature of the liquid mixture during the flowing and the collecting is maintained below 35° C., preferably below 30° C., more preferably below 25° C. to prevent acetalization. In one embodiment, yield of furanone production using the method of producing furanone is in the range of 10-99%, preferably 30-90%, more preferably 50-90%, even more preferably 65-90% most preferably about 85%, wherein yield is calculated based on the initial weight of the furfural.

In one embodiment, the method of producing the furanone compound further involves separating the furanone compound from the liquid mixture in a separator to form a furanone compound stream and a recycle stream. Separating as used herein refers to a process whereby the furanone compound is extracted from the liquid mixture by an extraction method such as distillation, chromatography, and/or liquid-liquid extraction. In one embodiment, the liquid mixture is first treated with an organic solvent (e.g. chloroform)

to form a solution, and the furanone compound is further extracted from the solution using a condenser, or a rotary evaporator. In another embodiment, the liquid mixture is treated with an organic solvent to form a two-phase liquid system. Accordingly, a furanone-containing phase may further be separated in a separatory funnel, and the furanone compound may be extracted from the furanone-containing phase. In one embodiment, the furanone compound stream is delivered to an auxiliary purification unit for further purification. In one embodiment, a purity of the furanone compound in the furanone compound stream is at least 90%, preferably at least 92%, or preferably at least 94%, or preferably at least 96%, or preferably at least 98%, or preferably at least 99% by volume. The furanone compound stream may comprise less than 10%, preferably less than 5%, more preferably less than 1% by volume of methanol, and/or water. In a preferred embodiment, the recycle stream has less than 10%, preferably less than 5%, more preferably less than 1% by volume of the furanone compound. In a preferred embodiment, at least a portion of the recycle stream is delivered to the vessel.

In one embodiment, the method of producing the furanone compound further involves stirring the liquid mixture in the vessel by an agitator present inside the vessel. In one embodiment, stirring the liquid mixture in the vessel is synced with flowing the liquid mixture. Accordingly, stirring the liquid mixture may begin by starting the flowing and ends by stopping the flowing. In another embodiment, the agitator stirs the liquid mixture for a limited duration, for example, for at least 5 min, preferably at least 10 min, or preferably at least 15 min and not more than 30 min.

Referring now to FIG. 1A. According to a second aspect the present disclosure relates to a photooxygenating system 100, involving the flow reactor 101 with the reaction section 102 having a first end and a second end and the mirror 104 located underneath the reaction section 102, wherein a reflecting side of the mirror faces the reaction section to enhance solar radiation 124.

The flow reactor as used herein refers to an apparatus comprising a tubular section (i.e. the reaction section), wherein the liquid mixture flowing through the tubular section is exposed to sunlight, and wherein one or more compounds in the liquid mixture are oxidized. In one embodiment, the flow reactor further comprises a plurality of liquid lines to fluidly connect the reaction section to a vessel. Accordingly, the reaction section 102 refers to a section of the flow reactor, wherein photooxygenation reaction takes place. In a preferred embodiment, the reaction section 102 is extended in the form of a spiral or coil to provide larger exposure area to solar radiation 124. In another preferred embodiment, the reaction section is planar spiral (i.e. folded back and forth on a plane) and the mirror is located underneath, wherein the mirror is parallel with the reaction section. In one embodiment, there is no gap between the mirror and the reaction section. In another embodiment, the mirror is located parallel to and within a distance from the reaction section, wherein the distance is in the range of 1-50 cm, preferably 10-20 cm, more preferably about 15 cm. In a preferred embodiment, the mirror is concaved to focus solar radiation 124 to a focal point, and concaved mirror is located within a distance from the reaction section such that the reaction section is at the focal point of the concaved mirror. In one embodiment, the reaction section comprises a plurality of spiral sections that are fluidly connected, wherein the mirror is located underneath the plurality of spiral sections. In a preferred embodiment, the mirror is located underneath the entire length of the reaction section.

In one embodiment, the reaction section is made of a transparent material. Exemplary transparent materials include, but are not limited to glass, general purpose polystyrene (GPPS), polycarbonate (PC), poly methyl methacrylate (PMMA), styrene acrylonitrile (SAN), styrene methyl methacrylate (SMMA), polyethylene terephthalate glycol-modified (PET-G), methyl metacrylate butadiene styrene (MRS), and/or any combination thereof. In a preferred embodiment, the reaction section is made of quartz. The reaction section may be tubular having an internal diameter of 0.1-2 cm, preferably 0.2-1 cm, more preferably 0.3-0.5 cm, even more preferably 0.3-0.4 cm, and a length of 5-200 cm, preferably 10-150 cm, or preferably 10-100 cm, or preferably 10-50 cm, or preferably 10-30 cm, or preferably 10-20 cm, or preferably about 15 cm. In one embodiment, the reaction section has an internal diameter of less than 0.5 cm, preferably less than 0.3 cm, more preferably less than 0.1 cm, and a length less than 30 cm, preferably less than 15 cm, more preferably less than 10 cm. In one embodiment, the reaction section is planar spiral (i.e. folded back and forth) having at least 3, preferably at least 5, more preferably at least 10, even more preferably at least 20 folded sections. In another embodiment, the reaction section is coiled having at least 3, preferably at least 5, more preferably at least 10, even more preferably at least 20 coils. In one embodiment, the reaction section comprises a plurality of coiled sections that are fluidly connected, wherein each coiled section has at least 3, preferably at least 5, more preferably at least 10, even more preferably at least 20 coils.

In one embodiment, the reaction section has a total volume capacity in the range of 0.001-600 cm$^3$, preferably 0.01-50 cm$^3$, or preferably 0.1-10 cm$^3$, or preferably 0.5-5 cm$^3$. In one embodiment, less than 20%, preferably less than 15%, or preferably less than 10%, or preferably less than 5%, or preferably less than 3% of the total volume of the liquid mixture is present in the reaction section at any given moment.

The photooxygenating system 100 further involves a vessel 108 with an internal cavity, a liquid inlet port 112, and a liquid outlet port 110, wherein the liquid outlet port is fluidly connected to the first end of the reaction section via a first liquid line 120, and the liquid inlet port is fluidly connected to the second end of the reaction section via a second liquid line 118.

Vessel as used herein refers to a container that is designed to hold a liquid preferably at temperatures and pressures near ambient temperature (i.e. 25° C.) and ambient pressure (1 atm). The vessel 108 may be made of glass, stainless steel, nickel steel, chromium steel, aluminum, aluminum alloy, copper and copper alloys, titanium, combinations thereof and the like, although the materials used to construct the vessel are not meant to be limiting and various other materials may also be used. In a preferred embodiment, an illuminance received by the liquid mixture inside the vessel is less than 0.001 lux, preferably less than 0.0001 lux, more preferably less than 0.00001 lux. In another embodiment, an irradiance received by the liquid mixture inside the vessel is less than 750 W/m$^2$, preferably less than 500 W/m$^2$, and more preferably less than 300 W/m$^2$.

In one embodiment, the vessel 108 has an internal volume in the range of 0.01-10,000 l, or preferably 0.01-100 l, or preferably 0.01-10 l, or preferably 0.05-1 l, or preferably 0.05-0.5 l. The vessel may also have other geometries including, but not limited to conical, rectangular, and pyramidal. In a preferred embodiment, the vessel has a cylindrical geometry which is vertically oriented.

In a preferred embodiment, a temperature control system is adapted to regulate temperature of the liquid mixture in the vessel. The temperature control system may comprise a temperature measurement device, a heating/cooling module, and a computer. The temperature measurement device may be a thermometer or preferably a thermocouple. The heating/cooling module may be a heat exchanger that is secured on and in direct contact with the external surface of the vessel. In one embodiment, the heating/cooling module is an elongated conduit which is helically extended around the circumference and along the length of the vessel, wherein a heating/cooling medium is circulated in the elongated conduit. According to this embodiment, the heating/cooling module covers 10-100%, preferably 50-90%, more preferably 50-80% and most preferably about 70% of the external surface area of the vessel. Alternatively, in another embodiment, the heating/cooling module is a plate located underneath the vessel and is in direct contact with the bottom end of the vessel.

In one embodiment, an agitator 114 is located inside the vessel to stir the liquid mixture 122. The agitator may be a mechanical stirrer, such as a propeller that is attached to a rotary motor 116 through a shaft. In one embodiment, the agitator is a magnetic stirrer. In another embodiment, the agitator rotates with a rotatory speed of at least 100 rpm, preferably at least 200 rpm, or preferably at least 300 rpm, or preferably at least 400 rpm, or preferably at least 500 rpm, or preferably at least 600 rpm.

The photooxygenating system 100 further involves a pump 106 for delivering the liquid mixture 122 from the vessel 108 to the reaction section 102, and returning the liquid mixture 122 to the vessel 108. The pump may be centrifugal, rotatory, or positive displacement. In a preferred embodiment, a flow-rate control system is adapted to regulate the flow rate of the liquid mixture through the reaction section. The flow-rate control system may comprise a valve, an actuator, and a computer.

In one embodiment, the liquid inlet 112 and the liquid outlet ports 110 are adapted for loading and unloading the vessel 108 with the liquid mixture 122. In one embodiment, the liquid inlet port 112 and the liquid outlet port 110 are substantially similar, wherein each is a cylindrical nozzle having an internal diameter in the range of 1-50 mm, preferably 1-10 mm, more preferably 1-5 mm, and configured to transfer the liquid mixture in the flow rate range of 0.5-50 ml/min, preferably 1-30 ml/min, more preferably 10-30 ml/min, even more preferably about 20 ml/min. In another embodiment, the liquid inlet 112 and the liquid outlet ports 110 are located proximal to the bottom of the vessel. In a vertically oriented cylindrical vessel, "proximal to the bottom" refers to a region of the vessel that is located less than 50%, preferably less than 40%, more preferably less than 30% of the height of the vessel when measured from the bottom of the vessel, with 0% being the bottom and 100% being the top of the vessel.

In one embodiment, the first 120 and the second liquid lines 118 are tubular channels that are configured to transport a liquid throughout the photooxygenating system 100. In one embodiment, inner diameter of the first and the second liquid lines are substantially similar to the inner diameter of the reaction section which is in the range of 0.1-2 cm, preferably 0.2-1 cm, more preferably 0.3-0.5 cm. In one embodiment, the liquid lines are substantially similar and are constructed from an opaque material such as a metal or an alloy that is coated with a polymer (e.g. epoxy).

In one embodiment, the photooxygenating system 100 further involves a separator 130 which is fluidly connected to a discharge port 132 of the vessel 108 via a discharge line 134, wherein the separator is configured to separate the furanone compound from the liquid mixture. In one embodiment, a valve is adapted on the discharge port 132. In one embodiment, the discharge line is substantially similar to the first and the second liquid lines. In another embodiment, the discharge port is substantially similar to the liquid inlet and the liquid outlet ports, wherein the discharge port is preferably located at the bottom end of the vessel. The separator may be a liquid-liquid extractor, a separatory funnel, a condenser, a distillation column, a rotary evaporator, or any combination thereof. In one embodiment, the separator is a rotary evaporator which operates at a temperature in the range of 40-80° C., preferably 50-60° C., more preferably 55° C., and at a rotary speed of 50-100 rpm, preferably 80-90 rpm, more preferably 85 rpm.

In one embodiment, in addition to oxidizing furfural, the photooxygenating system 100 can be adapted to oxyaminate/photo-oxidize alkyl aldehydes, or cyclic aldehydes, or ketone to form alkyl ketones, cyclic ketones, carboxylic acids, ketal compounds, diketone compounds, or α-oxyaminated aldehydes or ketones. The cyclic aldehyde may be aryl aldehydes, such as benzaldehyde, or heterocyclic aldehydes.

For example, in one embodiment, the method is utilized for producing an α-oxyaminated compound using the flow reactor, wherein 700-800 mg, preferably 750-800 mg, more preferably about 780 mg of a free radical (e.g. 2,2,6,6-tetramethylpiperidine-1-oxyl or TEMPO) is mixed with 200-300 mg, preferably 230-270 mg, more preferably about 250 mg of a photosensitizer in 30-80 ml, preferably 40-60 ml, more preferably about 50 ml of a solvent to form a dye solution. The photosensitizer may be preferably Rose Bengal, whereas the solvent is one selected from the group consisting of water, acetonitrile, and dichloromethane. In on embodiment, 500-1,200 µl, preferably 800-1,000 µl, more preferably about 900 µl ml of a ketone compound (e.g. ethyl benzoylacetate) is dissolved in the dye solution. In one embodiment, the dye solution is passed through the reaction section of the flow reactor, wherein the dye solution is exposed to solar radiation and the free radical and the ketone compound turn into the α-oxyaminated compound via a photo-induced α-oxyamination reaction. During the photo-induced α-oxyamination reaction, the photosensitizer may be excited under solar radiation and thus turning into a reductant. The reductant may transfer an electron to the ketone compound (e.g. ethyl benzoylacetate) to form a radical, which may further be coupled with the free radical (e.g. 2,2,6,6-tetramethylpiperidine-1-oxyl or TEMPO) to form the oxyaminated compound. In one embodiment, yield of producing the α-oxyaminated compound in the photo-induced α-oxyamination reaction is in the range of 50-99%, preferably 80-95%, more preferably 90-95%, wherein yield is calculated based on the initial weight of the ketone compound. In a preferred embodiment, water is used as the solvent, wherein yield of producing the α-oxyaminated compound in the photo-induced α-oxyamination reaction is in the range of 85-99%, preferably 85-95%, more preferably about 90%.

The examples below are intended to further illustrate protocols for the photooxygenating, and are not intended to limit the scope of the claims.

Example 1

The chemicals employed in this work were of analytical grade and were used as purchased. Ethanol, hydrochloric acid (37%) and Rose Bengal (RB) were purchased from Sigma-Aldrich Canada Ltd. (Oakville, Canada). Acetic acid (99.7%) and methanol were secured from Fisher Scientific (Pennington, N.J.). The water used in all treatments and analyses was high purity Milli-Q water (18 MV) obtained from Milli-Q water purification system (Millipore, Milford, Mass.).

Rice husk used in this study was provided by Chirackal agro mills Chirackal modern rice mill (Kerala, India). They were washed thoroughly with distilled water in a 2 L measuring cylinder, dried at 105° C. for over 12 h and then pulverized to pass through a 1 μm mesh screen for further use.

Example 2

The acid-catalyzed conversion of rice husk into furans was evaluated using three different isolation methods namely; a two-stage process involving microwave-assisted isolation [O. Yemiş, G. Mazza, Optimization of furfural and 5-hydroxymethylfurfural production from wheat straw by a microwave-assisted process, Bioresour. Technol. 109 (2012) 215-223], reflux method reported by Ong and Sashikala [H. K. Ong, M. Sashikala, Identification of furfural synthesized from pentosan in rice husk, J. Trop. Agric. Food Sci. 35 (2007) 305-312] and autoclave extraction method reported by Suxia et al. [R. Suxia, X. Haiyan, Z. Jinling, L. Shunqing, H. Xiaofeng, L. Tingzhou, Furfural production from rice husk using sulfuric acid and a solid acid catalyst through a two-stage process, Carbohydr. Res. 359 (2012) 1-6] as described.

Autoclave-assisted conversion method: A sample of pulverized rice husk (8.0 g) and 100 ml $H_2SO_4$ (1.0 M) were mixed and packed into 500 ml stainless steel autoclave with a Teflon® inner lining for acid hydrolysis. The packed vessels were sealed at both ends with circular cellulose filters and end caps, and then placed into a pre-heated oven for 7 h to hydrolyze pentosan present in the rice husk. After the preset time, the autoclave was removed and cooled down to room temperature. The resultant solid-liquid mixture was then filtered. A portion of the filtrate (50 ml) was further dehydrated by mixing it with 3.0 g of functionalized solid acid catalyst (SBA-15) into the autoclave followed by simultaneous addition of 150 ml of toluene. At the end of the reaction, the rice husk residues were filtered off leaving behind a two-layered mixture that was later separated using a separatory funnel into their respective components. Each extract was further concentrated using a rotary evaporator at 55° C. and 85 rpm rotating speed.

Reflux method: A reflux system consisting of 3.0 l capacity three-neck round bottom flask batch reactor, 30 cm Vigreux column, a condenser, a mechanical stirrer, extraction flask and a thermometer was used. Pulverized rice husk (265 g) and NaCl (400 g) were mixed and introduced into the batch reactor followed by 1.5 l HCl (1 M). A Vigreux column and a condenser were connected, and the reaction mixture was heated while stirring with a mechanical stirrer. Steam distillation was achieved after 15 min at a distilling temperature of 107° C. The distillate was set to flow into an extraction flask containing 250 ml chloroform. Two layers were formed with the aqueous layer at the top and the furfural-containing chloroform layer at the bottom of the flask. Pure furfural was isolated from non-aqueous solution using rotary evaporator at temperature below 40° C. with chloroform distilling off first.

Microwave-assisted conversion method: Acid-catalyzed conversion by microwave energy was carried out by means of a Multiwave 3000 (Anton Paar, Graz, Austria) equipped with 16 high-pressure polytetrafluoroethylene (PTFE) 100 ml vessels. Rice husk sample (1.0 g) was accurately weighed into each Teflon extraction vessel, acidified with 20.0 ml of 0.1 M hydrochloric acid and the reaction mixture was homogenized with a magnetic stirrer for 4 min before being transferred to the microwave oven. To ensure complete homogeneity of the reaction mixture, continuous stirring was maintained using a magnetic stir bar. The microwave system was temperature-controlled with a fiber temperature sensor. A temperature program with a preset temperature, cooling time, ramp temperature and residence time was defined using the system software version v1.52 aiming at maximizing the furfural yield. A ramp time of 10 min for reaching the target temperature (180° C.) was used in all subsequent treatments. The temperature was then kept constant for 20 min during the residence time followed by cooling to 28° C. in 40 min. After microwave treatment, it was noticed that the non-aqueous layer was smaller than the aqueous layer, and as a result, the solution mixture was transferred to a separatory funnel, and furfural was obtained by liquid-liquid extraction using chloroform as an extracting solvent. The resultant non-aqueous part was later tested and found to contain furfural, and was further refined using a rotary evaporator. However, as the temperature was increased above 180° C., there was a marked decrease in the furfural yield possibly due to self and cross polymerization reactions that compromise the acid conversion process [O. Yemiş, G. Mazza, Optimization of furfural and 5-hydroxymethylfurfural production from wheat straw by a microwave-assisted process, Bioresour. Technol. 109 (2012) 215-223].

With cross polymerization, the isolated furfural reacts with the intermediates in the reaction mixture leading to furfural loss while self-polymerization involves reaction of furfural with itself. Furfural was the major product obtained from acid catalyzed conversion of rice husks by the microwave-assisted process and was obtained as a clear yellowish liquid. The properties of furfural are summarized in the Table 1.

TABLE 1

Some general furfural properties [J. R. Dontulwar, R. Singru, I. A. Sayyad, Quantitative synthesis of furfural from waste material rice husk - a review, Int. J. Pharm. Sci. Rev. Res. 14 (2012) 4-9]

| | |
|---|---|
| Molecular weight | 96.1 |
| Freezing point (° C.) | −36.5 |
| Boiling point (° C.) | 161.7 |
| Density at 25° C. | 1.5 |
| Viscosity at 25° C. | 798.2 |
| Critical pressure (psi) | 398.2 |
| Critical temperature (° C.) | 397.4 |
| Heat of combustion at 25° C. (kcal/g mol) | −560.3 |
| Heat of formation (liquid at 25° C.) (kcal/g mol) | −49.2 |
| Heat of fusion (kcal/g mol) | 3.43 |

Example 3

The furfural content obtained from rice husk after the three acid catalyzed treatment processes was analyzed by gas chromatography-mass spectrometer (GC-MS) and fourier transform infrared spectrometer (FTIR).

A gas chromatograph (Agilent technologies, 6890N GC) coupled with a mass spectrometer (Agilent technologies, 5975B MSD) and HP-1 methyl siloxane column (Agilent 19091Z-213; 30 m×320 µm I.D.×1 µm thickness) was used. High purity helium (>99.999%) was used as a carrier gas and the samples were analyzed in a constant flow at 1.2 ml·min$^{-1}$. The temperature program used for the analyses was as follows: the initial temperature was held at 40° C. for 1 min which was then increased to 118° C. at 10° C.·min$^{-1}$ and held for 3 min then to 190° C. at 15° C.·min$^{-1}$ and held for 7 min. The injection port, ion source and interface temperatures were 280° C., 230° C., and 250° C., respectively. For quantitative determinations, selective ion monitoring mode was used.

Horizontal attenuated total reflectance (HAIR) method using zinc selenide crystal with density of 5.27 g/cm$^3$ was carried out in FTIR analyzer (PerkinElmer Co., USA). Transmission rate used was at 17,000-650 cm$^{-1}$. Acetone was used as a cleaning and diluting agent. Absorption spectra were registered using a Hewlett Packard 8453 UV-vis spectrophotometer (Palo Alto, Calif., USA).

Example 4

The yield of furfural from rice husk was compared using three different acid catalyzed isolation methods. Furfural yield is dependent on pentosan content in agricultural residues, and furfural is considered as a major decomposition product of pentoses [H. K. Ong, M. Sashikala, Identification of furfural synthesized from pentosan in rice husk, J. Trop. Agric. Food Sci, 35 (2007) 305-312]. When the external standard concentrations were plotted versus average peak areas, a linear fit with $R^2$=0.9997 and Y=26544X were generated. To quantify the furfural generated from the three different extracts, the corresponding peak areas were used to determine the furfural concentration in mg/l that was later used to compute the furfural yield. The furfural yield from rice husk was calculated as:

$$\% \text{ furfural yield} = \frac{\text{weight of furfural formed }(g)}{\text{dry weight of substrate utilized }(g)} \times 100$$

Figure 3:
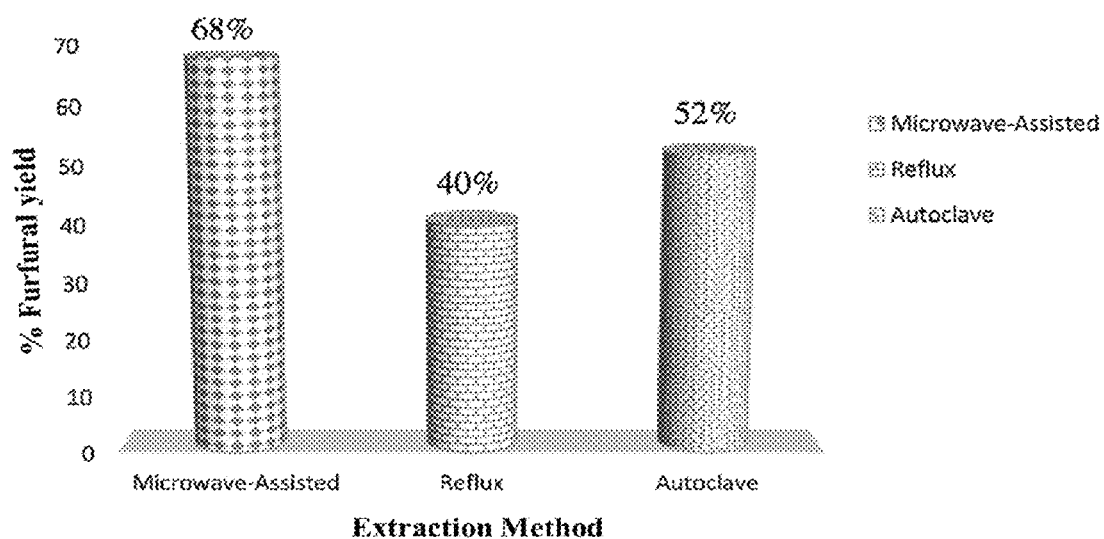
FIG. 3 represents a percentage of furfural yield from rice husk using three different extraction methods.

FIG. 3 summarizes the results of the percentage furfural that was generated from rice husk using different isolation methods.

Example 5

The yield of furfural from rice husk is dependent of isolation method used and the operating conditions including acid catalyst type, heating rate, residence time, temperature, substrate concentration and concentration of the catalyst [A. A. Peterson, F. Vogel, R. P. Lachance, M. Fröling, M. J. Antal Jr., J. W. Tester, Thermochemical biofuel production in hydrothermal media: a review of sub- and supercritical water technologies, Energy Environ. Sci. 1 (2008) 32]. The results in FIG. 3 show that the yield of furfural by the microwave-assisted isolation was relatively better than that by reflux and autoclave methods. Dontulwar et al. reported that, yield loss reactions during furfural production occur when furfural in the liquid phase undergoes further reaction with the pentose precursor and by polymerization [J. R. Dontulwar, R. Singru, I. A. Sayyad, Quantitative synthesis of furfural from waste material rice husk a review, Int. J. Pharm. Sci. Rev. Res. 14 (2012) 4-9]. Probably, the low yield of furfural by reflux and autoclave methods is due to 'entropy effect' resulting from increasing temperature that creates an environment of furfural disintegration that in turn inhibits the build-up of larger molecules [J. R. Dontulwar, R. Singru, I. A. Sayyad, Quantitative synthesis of furfural from waste material rice husk—a review, Int. J. Pharm. Sci. Rev. Res. 14 (2012) 4-9]. The furfural obtained was in liquid state and was colorless immediately after the microwave-assisted isolation, but turned yellowish and finally brown on exposure to light and air after a long period.

The IR-spectrum (figure not shown) shows a very strong absorption at 1730.46 cm$^{-1}$ corresponding to conjugated carbonyl group (C=O). The existence of two peaks at 3019.55 cm$^{-1}$ and 2881.87 cm$^{-1}$ further prove the presence of the aldehyde group. These absorptions show an aldehyde C—H intense stretching resulting from the Fermi resonance with the first overtone of the corresponding bending vibration that appear at 1367.41 cm$^{-1}$ in the spectrum. These bands are normal characteristics of aldehyde groups. The strong peaks observed from 1521.45 cm$^{-1}$ to 1421 cm$^{-1}$ are indicative of aromatic C=C bonds whereas =C—H bending out of plane appears from 928.7 cm$^{-1}$ to 849.5 cm$^{-1}$. The two strong peaks at 1166 cm$^{-1}$ and 1214.5 cm$^{-1}$ are characteristic of the C—O stretching vibration.

Figure 4:
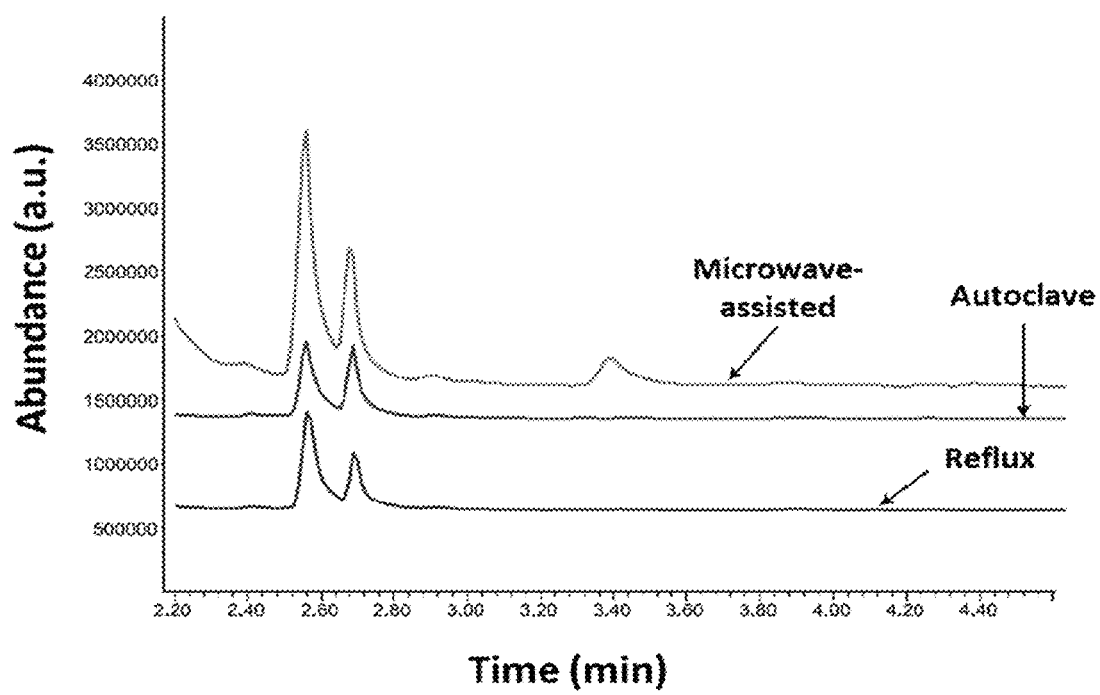
FIG. 4 represents GC-MS chromatograms of a furfural compound solution when extracted from rice husk using three different extraction methods.

The GC-MS chromatogram (FIG. 4) shows an overlay of the three furfural isolation methods (retention time of 2.72 min with a relative abundance of 100%). A molecular ion peak is at m/z 96.0 that correlates well with the molecular formula of furfural and a peak at m/z 95.2 due to hydrogen loss from furfural to form a carbonium ion (spectrum not shown). This fragmentation is due to the formation of a more stable cation resulting from loss of hydrogen atom. It is clear from the overlaid chromatogram that microwave-assisted isolation method generates a relatively better furfural yield compared to the other methods.

Example 6

A number of innovative strategies have been developed to increase synthetic efficiency [K. C. Nicolaou, D. J. Edmonds, P. G. Bulger, Cascade reactions in total synthesis, Angew. Chemie—Int. Ed. 45 (2006) 7134-7186]. A simple continuous flow quartz capillary microreactor was developed and used to investigate the photochemical potential of furfural for small scale synthesis of 5-hydroxy-2-(5H)-furanone which is an important synthon in organic synthesis.

Figure 1B:
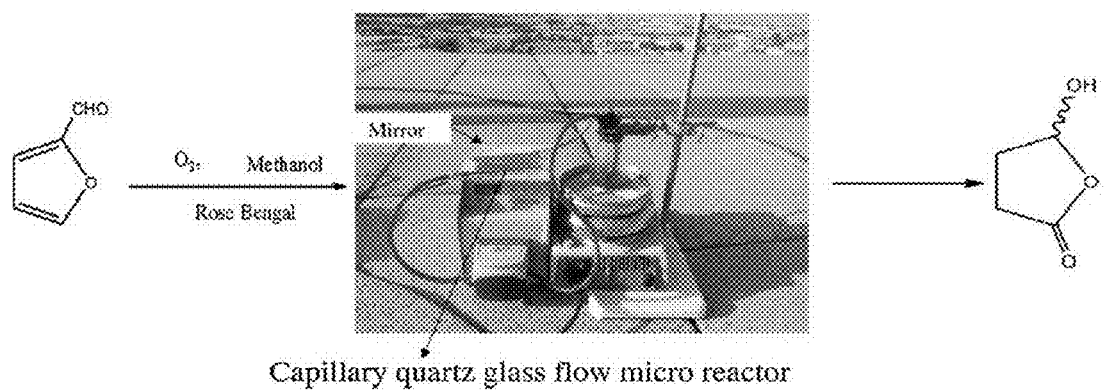
FIG. 1B illustrates the flow reactor during operation.

The experimental set-up (FIG. 1B) consisted of a quartz glass-loop flow microreactor, a magnetic stirrer, a 125 ml Erlenmeyer flask, a reflecting mirror, reactor capillary tubes and a peristaltic pump. The reactor had an inner diameter of 0.3 cm and a total length of 15 cm. The mirror placed below the quartz microreactor to maximize the sunlight intensity through reflection, and the pump was to allow continuous flow of the reactant mixture through the reactor.

Example 7

This experimental set-up was used in photooxygenation reactions involving the isolated furfural from rice husk using RB as a photosensitizer in methanol with sunlight irradiation. All solar irradiation experiments were performed on roof-top of a building during the months of February, March and April. The daily maximum global radiation ranged from 300 W/m$^2$ to 850 W/m$^2$. A solution consisting of freshly distilled furfural (0.8 ml), RB (0.91 g) dissolved in methanol (50 ml), and a stirring bar was added to a reaction flask. The reaction mixture was kept at a temperature below 35° C. to prevent acetalization during photooxygenation reaction [A. Gassama, C. Emenwein, N. Hoffmann, Photochemical key steps in the synthesis of surfactants from furfural-derived intermediates, ChemSusChem 2 (2009) 1130-1137]. The mixture was irradiated under direct sunlight for 2, 4, 6, 8 and 12 h via a quartz capillary flow reactor while purging with a gentle stream of air using an air pump. The reaction was monitored by withdrawing aliquots of sample solution from the reaction flask after a given period of time using a syringe, chromatographed on silica gel and the collected fractions analyzed by GC-MS. The experiment was then varied for maximum efficiency by varying different experimental conditions. Percentage conversion was calculated using the formula below.

$$\% \text{ conversion} = \left[\frac{P_0 - P_t}{P_0}\right] \times 100$$

Wherein $P_o$ is the peak area of the limiting reactant at the start of the experiment, and $P_t$ is the peak area of the limiting reactant that remained at the end of the experiment, while % furanone yield was calculated as a product of selectivity and % conversion.

Example 8

Figure 5:
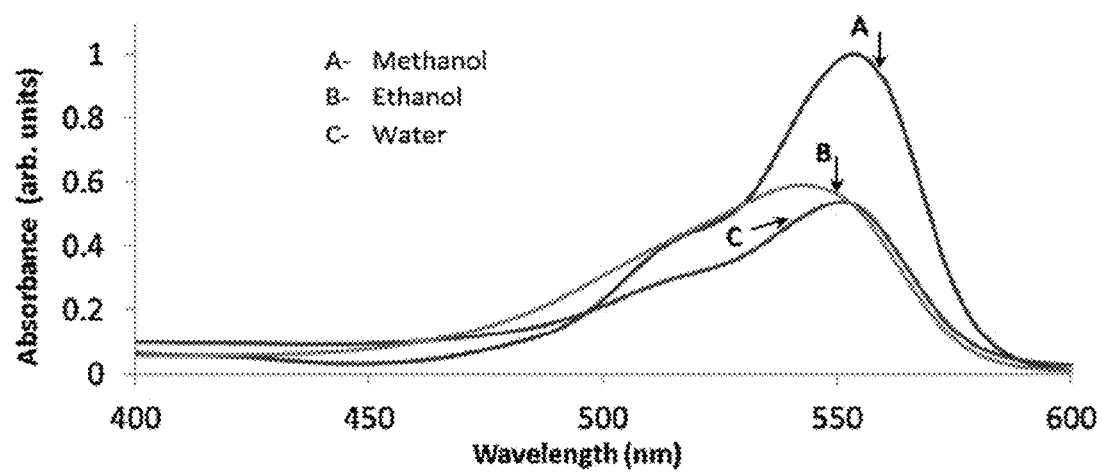
FIG. 5 represents UV spectra of rose Bengal dissolved in three different reaction solvents.

To determine the effect of solvent media for dissolving RB, three different solvents were investigated (water, methanol and ethanol) and UV scans were taken for the samples as shown in FIG. 5. RB in methanol gave a higher absorption than the rest of the solvents.

Investigations of sunlight irradiation and RB sensitizer were performed in an effort to understand the influence of these parameters on the photooxidation of furfural. Control experiments were conducted in a dark room where the set-up was fully covered with aluminium foil throughout the experimental period. To investigate the role of RB in this experiment, similar experiments were prepared and irradiated with sunlight but without the RB sensitizer. All experiments were conducted in triplicate, and the averages and deviations associated with each average are summarized in Tables 2-5.

TABLE 2

Effect of mass of Rose Bengal sensitizer on dye-sensitized photooxygenation of furfural in continuous flow microreactor (RB present and 4 h sunlight irradiation)

| Expt no. | Mass of RB (g) | Â % Yield, n = 3 |
| --- | --- | --- |
| 1 | 0 | 0.0 |
| 2 | 0.2 | 38.00 ± 2.17 |
| 3 | 0.4 | 64.00 ± 3.07 |
| 4 | 0.8 | 68.00 ± 2.92 |
| 5 | 1 | 77.00 ± 1.15 |
| 6 | 1.2 | 76.50 ± 0.18 |
| 7 | 1.5 | 74.60 ± 1.67 |
| 8 | 2 | 70.50 ± 2.80 |
| 9 | 2.4 | 68.80 ± 1.45 |

TABLE 3

Effect of time on the dye-sensitized photooxygenation of furfural in continuous flow microreactor (1 g RB)

| Expt no. | Time (h) | % Yield, n = 3 |
| --- | --- | --- |
| 10 | 2 | 48.00 ± 4.50 |
| 11 | 4 | 65.00 ± 3.65 |
| 12 | 6 | 84.00 ± 2.42 |

TABLE 3-continued

Effect of time on the dye-sensitized photooxygenation of furfural in continuous flow microreactor (1 g RB)

| Expt no. | Time (h) | % Yield, n = 3 |
| --- | --- | --- |
| 13 | 8 | 84.10 ± 2.60 |
| 14 | 10 | 84.00 ± 0.98 |
| 15 | 12 | 84.10 ± 0.78 |

TABLE 4

Photooxygenation of furfural under different conditions

| Expt no. | Sensitizer (RB) | Irradiation | Â % Yield SD (n = 3) |
| --- | --- | --- | --- |
| 16 | Present | Shade | 10.0 ± 4.67 |
| 17 | Present | Shade | 9.0 ± 2.40 |
| 18 | Present | Dark | 0.0 |
| 10 | Absent | Yes | 0.0 |
| 20 | Absent | Yes | 0.0 |
| 21 | Absent | Yes | 0.0 |

TABLE 5

Photooxygenated reactions under different weather conditions (RB, MeOH solvent, and 6 h irradiation time)

| Expt no. | Sensitizer | Solvent | Sunlight conditions | Time (h) | % Yield, n = 3 |
| --- | --- | --- | --- | --- | --- |
| 22 | RB | MeOH | Complete cloud cover | 6 | 34.0 ± 3.30 |
| 23 | RB | MeOH | Direct sun | 6 | 84.0 ± 2.45 |
| 24 | RB | MeOH | Partial cloud | 6 | 72.0 ± 1.90 |

Example 9

Figure 6:
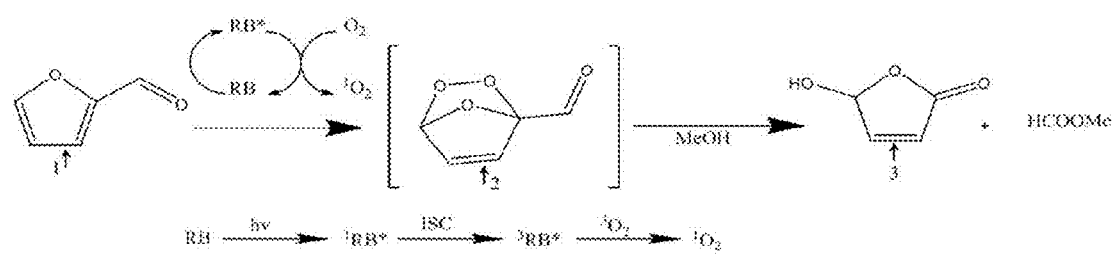
FIG. 6 represents a proposed reaction mechanism for conversion of furfural to a furanone compound.

Taking the advantage of continuous flow reactor, the efficiency of the reaction shown in FIG. 6 improved significantly. With such reaction set-up, the reaction yield was enhanced as well. The photooxygenation of furfural 1 is believed to follow a concerted 4+2 cycloaddition with the initial addition of singlet oxygen to form an unstable endoperoxide 2 which in presence of methanol forms 5-hydroxy-2-(5H)-furanone 3 as shown in Scheme 2 [A. Gassama, C. Ernenwein, N. Hoffmann, Photochemical key steps in the synthesis of surfactants from furfural-derived intermediates, ChemSusChem 2 (2009) 1130-1137].

Figure 7:
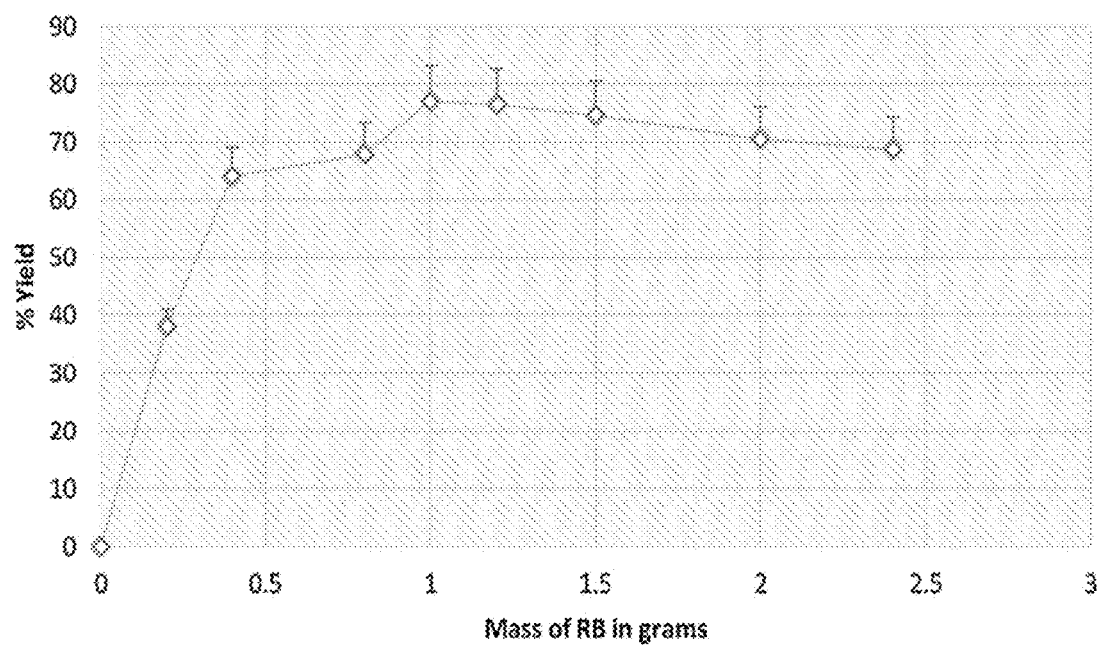
FIG. 7 depicts production yields of the furanone compound from furfural with respect to mass of rose Bengal, at constant sunlight exposure time.
Figure 8:
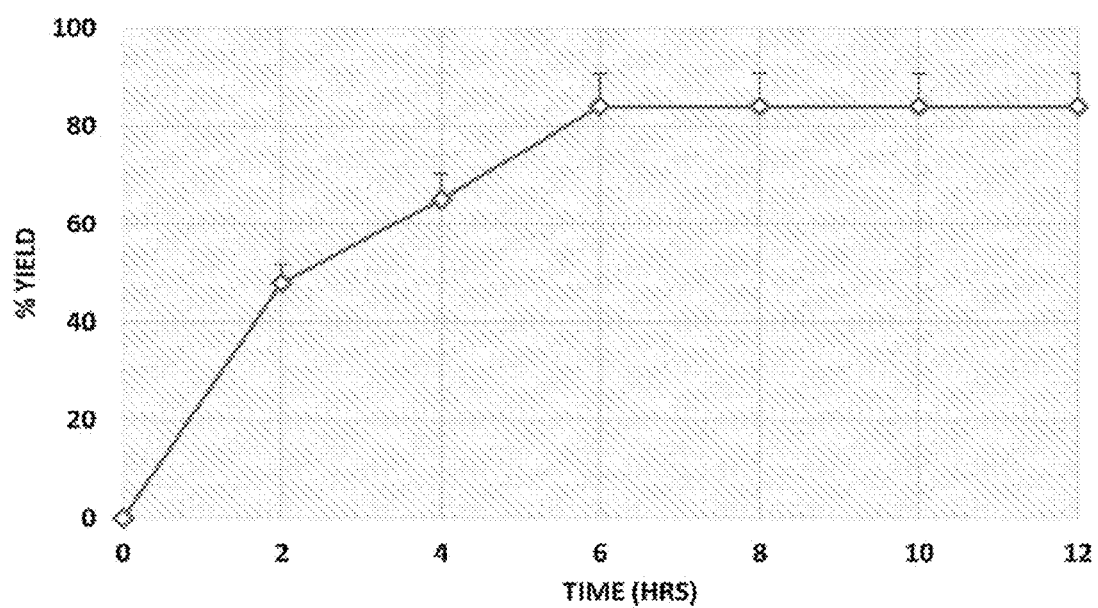
FIG. 8 depicts production yields of the furanone compound from furfural with respect to sunlight exposure time, at constant mass of rose Bengal.

The plot in FIG. 7 shows that the percentage yield of furanone 3 increases with increase in the mass of the photosensitizer, reaches a maximum value and then reduces. This is because photo-oxygenation Reactions obey Beer's law in which the reaction mixture must not be concentrated to the extent that prevents light penetration. In absence of a photosensitizer, no conversion takes place at all. Maximum furanone yield in FIG. 8 was realized after an irradiation time of 6 h. This trend might be due to the limiting reactant being used up.

The results in Tables 2-5 demonstrate that the furanone yield is highly dependent on the presence and quantity of RB sensitizer. RB is highly soluble in polar solvents making it an ideal candidate for use as a sensitizer for dye-sensitized photooxygenation. In addition, it absorbs strongly within the visible region which further makes it an ideal sensitizer when using solar light. It is also well known as being a singlet oxygen sensitizer [H. Liu, W. Feng, C. W. Kee, Y. Zhao, D. Leow, Y. Pan, et al., Organic dye photocatalyzed α-oxyamination through irradiation with visible light, Green Chem. 12 (2010) 953]. Sensitizer-free experiments (entries 19, 20, and 21) show that furfural does not self-sensitize to products. Experiments 16, 17 and 18 showed loss in efficacy in absence of sun light.

In direct sunlight (entry 23), 84% 5-hydroxy-2-(5H)-furanone yield was realized while under the conditions of partial cloud and partial sun (entries 22 and 24), a yield of 34-72% was obtained. These results are as anticipated since much more photons are generated in direct sunlight that will facilitate sensitizer excitation leading to generation of more singlet oxygen that constitutes a key factor in furfural photooxygenation reaction.

Acid-catalyzed conversion of rice husk to furfural was evaluated using different isolation methods. Microwave-assisted method gave higher furfural yield than other methods. Using this method, self and cross polymerization of furfural are greatly minimized. Moreover, it is envisioned to be a greener and faster isolation method since its operations do not involve organic solvents. We also succeeded in developing a simple and effective capillary flow microreactor for photochemical applications of furfural to furanone.

The invention claimed is:

1. An acid treatment method to form a furanone compound from biomass, comprising:
   extracting furfural from rice husk with an acid treatment;
   mixing the furfural, at least one photosensitizer selected from the group consisting of Rose Bengal, Basic Blue 9, Rhodamine B, methylene blue, mesotetraphenylporphine, polyene dye 2-cyano-5-(4-dimethylaminophenyl)penta-2,4-dienoic acid, $Ru(byp)_3Cl_2$, and $Ru(byp)_3Cl_2$-imidazolidinone, and a reaction solvent in a vessel to form a liquid mixture; and
   flowing at least a portion of the liquid mixture through a reaction section of a flow reactor, while concurrently exposing the liquid mixture to sunlight to oxidize the furfural to form the furanone compound.

2. The method of claim 1, further comprising:
   collecting the liquid mixture in the vessel; and
   repeating the flowing and the collecting until the liquid mixture reaches a predetermined furanone concentration.

3. The method of claim 1, wherein the extracting comprises treating the rice husk with a mineral acid in a microwave.

4. The method of claim 1, wherein the extracting comprises hydrolyzing the rice husk with a mineral acid in an autoclave.

5. The method of claim 1, wherein the extracting comprises treating the rice husk with a mineral acid in a reflux system.

6. The method of claim 1, wherein a concentration of the photosensitizer in the liquid mixture is in the range of 4-40 g/l.

7. The method of claim 1, wherein the liquid mixture comprises 0.2-2.5 g of the photosensitizer per 1 ml of the furfural.

8. The method of claim 1, wherein the reaction solvent is at least one selected from the group consisting of water, methanol, ethanol, acetonitrile, dichloromethane, tetrahydrofuran, and toluene.

9. The method of claim 8, wherein the reaction solvent is methanol.

10. The method of claim 1, wherein a concave mirror is located under the reaction section, and wherein the concave mirror has a focal point for focusing sunlight onto the reaction section.

11. The method of claim 1, wherein the reaction section is exposed to sunlight for 2-12 hours.

12. The method of claim 1, wherein the reaction section of the flow reactor has a spiral shape.

13. The method of claim 1, further comprising:
   separating the furanone compound from the liquid mixture in a separator to form a furanone compound stream and a recycle stream; and
   delivering at least a portion of the recycle stream to the vessel.

14. The method of claim 1, further comprising:
   stirring the liquid mixture in the vessel with an agitator.

15. The method of claim 9, wherein the liquid mixture in the vessel is maintained at a temperature below 35° C. to prevent acetalization.

16. The method of claim 1, wherein the extracting includes treating the rice husks with at least one acid selected from the group consisting of hydrochloric acid, nitric acid, sulfuric acid and phosphoric acid.

* * * * *